(12) United States Patent
Takahashi

(10) Patent No.: US 11,191,512 B2
(45) Date of Patent: Dec. 7, 2021

(54) RADIOGRAPHIC IMAGE PROCESSING DEVICE AND RADIOGRAPHIC IMAGE PROCESSING METHOD

(71) Applicant: FUJIFILM Corporation, Tokyo (JP)

(72) Inventor: Tomoyuki Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 77 days.

(21) Appl. No.: 16/831,738

(22) Filed: Mar. 26, 2020

(65) Prior Publication Data
US 2020/0305830 A1 Oct. 1, 2020

(30) Foreign Application Priority Data

Mar. 29, 2019 (JP) .............................. JP2019-068088

(51) Int. Cl.
| | | |
|---|---|---|
| *G21K 1/12* | (2006.01) | |
| *A61B 6/00* | (2006.01) | |
| *G01T 1/20* | (2006.01) | |

(52) U.S. Cl.
CPC ............ *A61B 6/5282* (2013.01); *A61B 6/461* (2013.01); *A61B 6/483* (2013.01); *A61B 6/5205* (2013.01); *A61B 6/503* (2013.01)

(58) Field of Classification Search
CPC ... A61B 6/5282; A61B 6/4233; A61B 6/4266; A61B 6/544; A61B 6/505; A61B 6/5205; A61B 6/503; A61B 6/483; A61B 6/461; A61B 6/4291; G01T 1/2018
See application file for complete search history.

(56) References Cited

U.S. PATENT DOCUMENTS

2004/0264626 A1* 12/2004 Besson .................. A61B 6/563
378/4
2015/0379711 A1 12/2015 Imai

FOREIGN PATENT DOCUMENTS

| JP | 2014207958 | 11/2014 |
| JP | 2016172098 | 9/2016 |

\* cited by examiner

*Primary Examiner* — Don K Wong
(74) *Attorney, Agent, or Firm* — JCIPRNET

(57) ABSTRACT

A radiographic image processing device includes a radiographic image acquisition unit that acquires a radiographic image taken from a subject using radiation, a region discrimination unit that discriminates a plurality of regions using the radiographic image, a scattered radiation component-estimation section that estimates scattered radiation components of the radiation of each region using scattered radiation component-estimation processing varying for each region, a scattered radiation component-subtraction section that subtracts the scattered radiation components of each region, and an image processing unit that generates a scattered radiation component-subtracted image where the scattered radiation components have been subtracted by sequentially estimating and subtracting the scattered radiation components of each region using the scattered radiation component-estimation section and the scattered radiation component-subtraction section.

14 Claims, 9 Drawing Sheets

RADIOGRAPHIC IMAGE PROCESSING DEVICE AND RADIOGRAPHIC IMAGE PROCESSING METHOD

CROSS-REFERENCE TO RELATED APPLICATIONS

This application claims priority under 35 U.S.C. § 119(a) to Japanese Patent Application No. 2019-068088 filed on 29 Mar. 2019. The above application is hereby expressly incorporated by reference, in its entirety, into the present application.

BACKGROUND OF THE INVENTION

1. Field of the Invention

The present invention relates to a radiographic image processing device and an image processing method that perform image processing on a radiographic image.

2. Description of the Related Art

A radiographic imaging device imaging a subject using radiation, such as an X-ray, has been spread in the past. For example, in a case where a subject is a human or an animal, a radiographic image is used for the diagnosis or the like of a lesion.

It is desirable that a radiographic image is formed in radiographic imaging using only primary radiation directly transmitted through a subject and the like. However, in a case where radiation is incident on elements of the radiographic imaging device and/or a subject and the like, a part of the radiation is scattered and forms so-called scattered radiation. Components (hereinafter, referred to as scattered radiation components) generated in a radiographic image due to scattered radiation are noise. For this reason, a grid absorbing scattered radiation components is usually used at the time of imaging, and/or scattered radiation components are reduced by image processing performed after imaging.

There is image processing that is called, for example, virtual grid as the image processing for reducing scattered radiation components after imaging (JP2014-207958A (corresponding to US2015/379711A1) and JP2016-172098A). Virtual grid is image processing for obtaining a radiographic image where scattered radiation components have been reduced by estimating the quantity of scattered radiation components included in each pixel of the radiographic image using the thickness of a subject and subtracting the estimated quantity of scattered radiation components from an original radiographic image.

SUMMARY OF THE INVENTION

Image processing for reducing scattered radiation components included in a radiographic image has been known. However, in recent years, there has been a demand for a technique for estimating scattered radiation components with higher accuracy and reducing the scattered radiation components. The reason for this is to more accurately make a diagnosis and the like using a radiographic image.

Further, in recent years, there has been a case where not only radiographic images taken for diagnosis and the like are displayed but also a calculation and the like are made using radiographic images to provide a radiographic image in which some tissues and the like included in a subject are highlighted or information about the composition and the like of the subject. For example, radiographic images used for diagnosis and the like are not limited to so-called projection images, and there is a case where a soft part image where soft part tissues of a subject are extracted (or highlighted) and/or a bony part image where bony parts of a subject are extracted are used. The soft part image and/or the bony part image are generated by so-called subtraction processing. The subtraction processing is processing for giving predetermined weight to two types of radiographic images, which are different from each other in energy of radiation used for imaging and the like, and calculating a difference between the radiographic images; and is processing using an attenuation coefficient for radiation that varies according to composition. Further, there is a case where bone mineral content (bone density) is measured by calculation using, for example, the pixel values of a radiographic image.

In a case where a radiographic image is used for calculation as described above, scattered radiation components are particularly required to be reduced from the radiographic image used for calculation with high accuracy. The reason for this is that errors caused by scattered radiation components negatively affect calculation results and it is difficult to obtain accurate calculation results in a case where a calculation using a radiographic image is made.

An object of the invention is to provide a radiographic image processing device and a radiographic image processing method that can reduce the scattered radiation components of a radiographic image with higher accuracy than that in the related art by image processing.

A radiographic image processing device according to an aspect of the invention comprises a radiographic image acquisition unit that acquires a radiographic image taken from a subject using radiation, a region discrimination unit that discriminates a plurality of regions using the radiographic image, a scattered radiation component-estimation section that estimates a scattered radiation component of the radiation of each region using scattered radiation component-estimation processing varying for each region, a scattered radiation component-subtraction section that subtracts the scattered radiation component of each region, and an image processing unit that generates a scattered radiation component-subtracted image where the scattered radiation component has been subtracted by sequentially estimating and subtracting the scattered radiation component of each region using the scattered radiation component-estimation section and the scattered radiation component-subtraction section.

It is preferable that the radiographic image processing device further comprises a processing order determination unit determining an order of the regions in which the image processing unit estimates and subtracts the scattered radiation component.

It is preferable that the order is an order in which the region where the number of types of scatterers scattering the radiation is smaller is processed earlier.

It is preferable that, in a case where the region discrimination unit discriminates a direct region where the radiation directly reaches a radiation detector without being transmitted through the subject and a subject region where the radiation reaches the radiation detector through the subject, and the image processing unit generates a direct region-scattered radiation component-subtracted image by subtracting the scattered radiation component of the direct region from the radiographic image and generates a subject region-scattered radiation component-subtracted image by further subtracting the scattered radiation component of the subject region from the direct region-scattered radiation component-subtracted image.

It is preferable that the region discrimination unit divides the subject region into a bony part region including a bony part and a soft part region including a soft part tissue and discriminates the bony part region and the soft part region, and the image processing unit subtracts the scattered radiation component of the bony part region from the direct region-scattered radiation component-subtracted image and further subtracts the scattered radiation component of the soft part region from the direct region-scattered radiation component-subtracted image where the scattered radiation component of the bony part region has been subtracted.

It is preferable that the region discrimination unit divides the subject region into a bony part region including a bony part and a soft part region including a soft part tissue and discriminates the bony part region and the soft part region, and the image processing unit subtracts the scattered radiation component of the soft part region from the direct region-scattered radiation component-subtracted image and further subtracts the scattered radiation component of the bony part region from the direct region-scattered radiation component-subtracted image where the scattered radiation component of the soft part region has been subtracted.

It is preferable that the region discrimination unit divides the soft part region into regions according to composition and discriminates the divided regions.

It is preferable that the region discrimination unit discriminates a separation region where the subject is separated from a radiation detector taking the radiographic image.

It is preferable that the region discrimination unit discriminates an artifact region where an artifact mounted on the subject or included in the subject is present.

It is preferable that the region discrimination unit discriminates a region outside a region irradiated with radiation.

It is preferable that the radiographic image processing device further comprises a selection unit selecting the scattered radiation component-estimation processing for each region.

It is preferable that the selection unit automatically selects the scattered radiation component-estimation processing to be applied to the region using a position, a size, a shape, and/or a density of the region.

It is preferable that the selection unit accepts selection of the scattered radiation component-estimation processing to be applied to each region.

A radiographic image processing method according to another aspect of the invention comprises a radiographic image acquisition step of causing a radiographic image acquisition unit to acquire a radiographic image taken from a subject using radiation, a region discrimination step of causing a region discrimination unit to discriminate a plurality of regions using the radiographic image, a scattered radiation component-estimation step of causing a scattered radiation component-estimation section to estimate a scattered radiation component of the radiation of each region using scattered radiation component-estimation processing varying for each region, and a scattered radiation component-subtraction step of causing a scattered radiation component-subtraction section to subtract the scattered radiation component of each region; and the image processing unit sequentially estimates and subtracts the scattered radiation component for each region by performing the scattered radiation component-estimation step and the scattered radiation component-subtraction step for each region using the scattered radiation component-estimation section and the scattered radiation component-subtraction section, and generates a scattered radiation component-subtracted image where the scattered radiation component has been subtracted.

According to the radiographic image processing device and the radiographic image processing method of the aspects of the invention, it is possible to reduce the scattered radiation components of a radiographic image with higher accuracy than that in the related art by image processing.

DESCRIPTION OF THE PREFERRED EMBODIMENTS

First Embodiment

Figure 1:
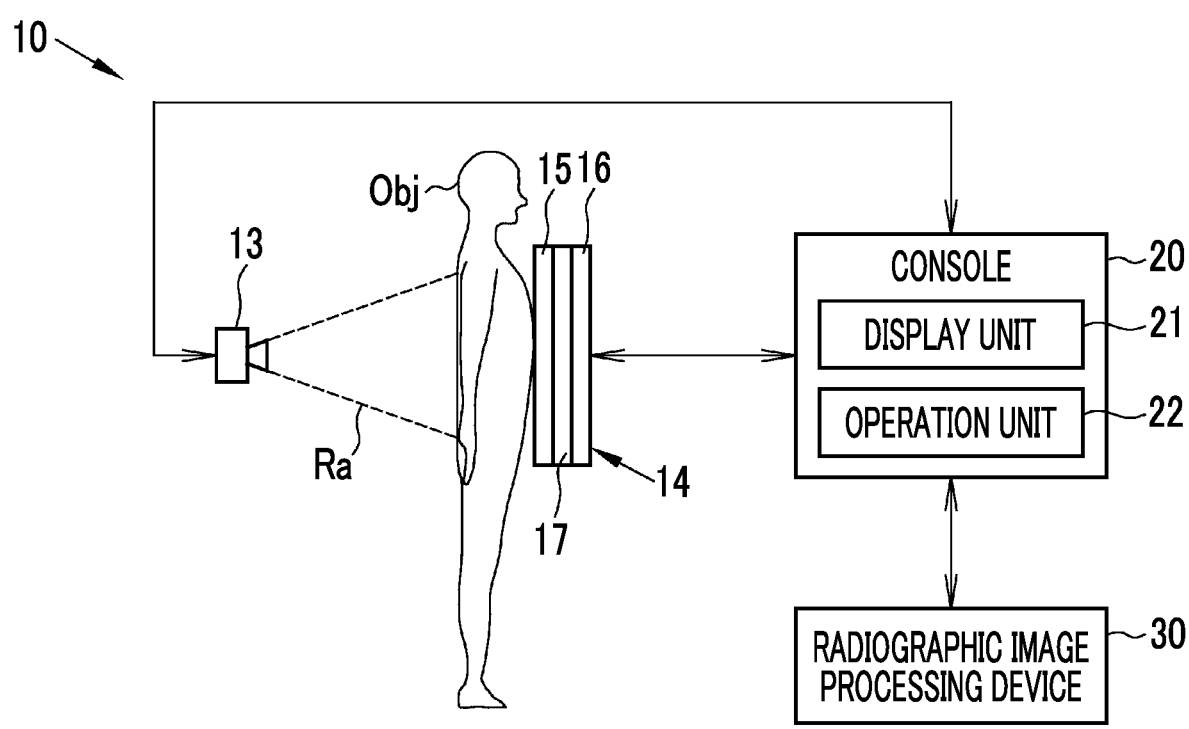
FIG. 1 is a diagram illustrating the configuration of a radiographic imaging device.

As shown in FIG. 1, a radiographic imaging system 10 comprises a radiation source 13, a radiographic imaging panel 14, a console 20, and a radiographic image processing device 30. The radiation source 13, the radiographic imaging panel 14, and the console 20 form a radiographic imaging device.

A radiation source 13 is a device generating radiation Ra required for imaging, and includes a radiation tube that generates the radiation Ra, a high voltage generating circuit that generates a high voltage required to allow the radiation tube to generate radiation Ra, and the like. The radiation source 13 can generate a plurality of types of radiation having different qualities (energy distributions (hereinafter, simply referred to as energy)) by adjusting the tube voltage and the tube current of the radiation tube, and the like. The energy of the radiation generated by the radiation source 13 is one of imaging conditions. In this embodiment, the radiation source 13 is an X-ray source generating an X-ray. For this reason, the radiographic imaging system 10 is an X-ray imaging system that acquires the X-ray image of a subject Obj by imaging the subject Obj using an X-ray. The subject Obj is, for example, a human.

The radiographic imaging panel 14 is a radiation detector that images the subject Obj using the radiation Ra generated by the radiation source 13. The radiographic imaging panel 14 is a so-called flat panel detector (FPD), and outputs the radiographic image of the subject Obj by detecting the radiation Ra, which is transmitted through the subject Obj, and converting the radiation Ra into electrical signals. In the imaging using the radiographic imaging panel 14, a grid (not shown) can be used together as necessary. The grid is a device for removing scattered radiation components of radiation, and is, for example, a stationary Lysholm grid, a movable Bucky's grid, or the like.

In this embodiment, the radiographic imaging panel 14 comprises two radiation detectors, that is, a first radiation detector 15 and a second radiation detector 16. One detector, which is disposed to be closer to the subject Obj and the radiation source 13, of the first and second radiation detectors 15 and 16 is the first radiation detector 15, and the other detector thereof, which is disposed to be farther from the subject Obj and the radiation source 13, is the second radiation detector 16. The first and second radiation detectors 15 and 16 detect the radiation Ra, which is transmitted through the subject Obj, of each pixel. Further, each of the first and second radiation detectors 15 and 16 outputs the radiographic image of the subject Obj. However, the radiographic imaging panel 14 comprises a radiation energy conversion filter 17 between the first and second radiation detectors 15 and 16. The radiation energy conversion filter 17 is, for example, a copper plate or the like, and absorbs the low-energy components of the radiation Ra. For this reason, the energy of the radiation Ra is changed until the radiation Ra reaches the second radiation detector 16 after being transmitted through the first radiation detector 15. Accordingly, the radiographic imaging panel 14 simultaneously images the specific subject Obj under the same imaging conditions (with the same radiation Ra), but a first radiographic image G1 (see FIG. 9) output by the first radiation detector 15 and a second radiographic image G2 (not shown since the second radiographic image G2 is the same as the first radiographic image G1) output by the second radiation detector 16 are radiographic images that are taken using radiation Ra having substantially different energies.

Each of the first and second radiation detectors 15 and 16 is any one of an indirect conversion type detector or a direct conversion type detector, or different types of detectors may be employed as the first and second radiation detectors 15 and 16. The indirect conversion type detector is a detector that converts the radiation Ra into visible light by using a scintillator made of cesium iodide (CsI) or the like and photoelectrically converts the visible light into electrical signals to indirectly obtain electrical signals. The direct conversion type detector is a detector that directly converts the radiation Ra into electrical signals by using a scintillator made of amorphous selenium or the like. Further, each of the first and second radiation detectors 15 and 16 may be a penetration side sampling (PSS) detector or may be an irradiation side sampling (ISS) detector. A PSS system is a system in which a scintillator is disposed on a side, which faces the subject Obj, of a thin film transistor (TFT) that read out electrical signals. An ISS system is a system in which a TFT and a scintillator are arranged in this order from the subject Obj on the contrary to the PSS system.

The console 20 is a control device (computer) for controlling the operations of the radiation source 13 and the radiographic imaging panel 14, and comprises a display unit 21, an operation unit 22, and the like. The display unit 21 is, for example, a liquid crystal display or the like, and displays necessary items according to operations, setting, or the like in addition to taken radiographic images. The operation unit 22 is, for example, a keyboard and/or a pointing device, or the like that are used for the setting input of imaging conditions and the like and the operation of the radiation source 13 and the radiographic imaging panel 14. The display unit 21 and the operation unit 22 can be formed of touch panels.

The radiographic image processing device 30 performs image processing using radiographic images, which are taken from the subject Obj, for display in diagnosis and the like or for detailed image analysis and the like according to diagnosis and the like. The radiographic image processing device 30 is directly connected to the console 20, and can acquire the radiographic images, which are taken from the subject Obj, in real time and use the radiographic images in image processing. Further, the radiographic image processing device 30 can indirectly acquire radiographic images through radiology information systems (RIS), hospital information systems (HIS), picture archiving and communication systems (PACS), a digital imaging and communications in medicine (DICOM) server included in PACS, or the like instead of being directly connected to the console 20 and use the radiographic images in the image processing.

Figure 2:
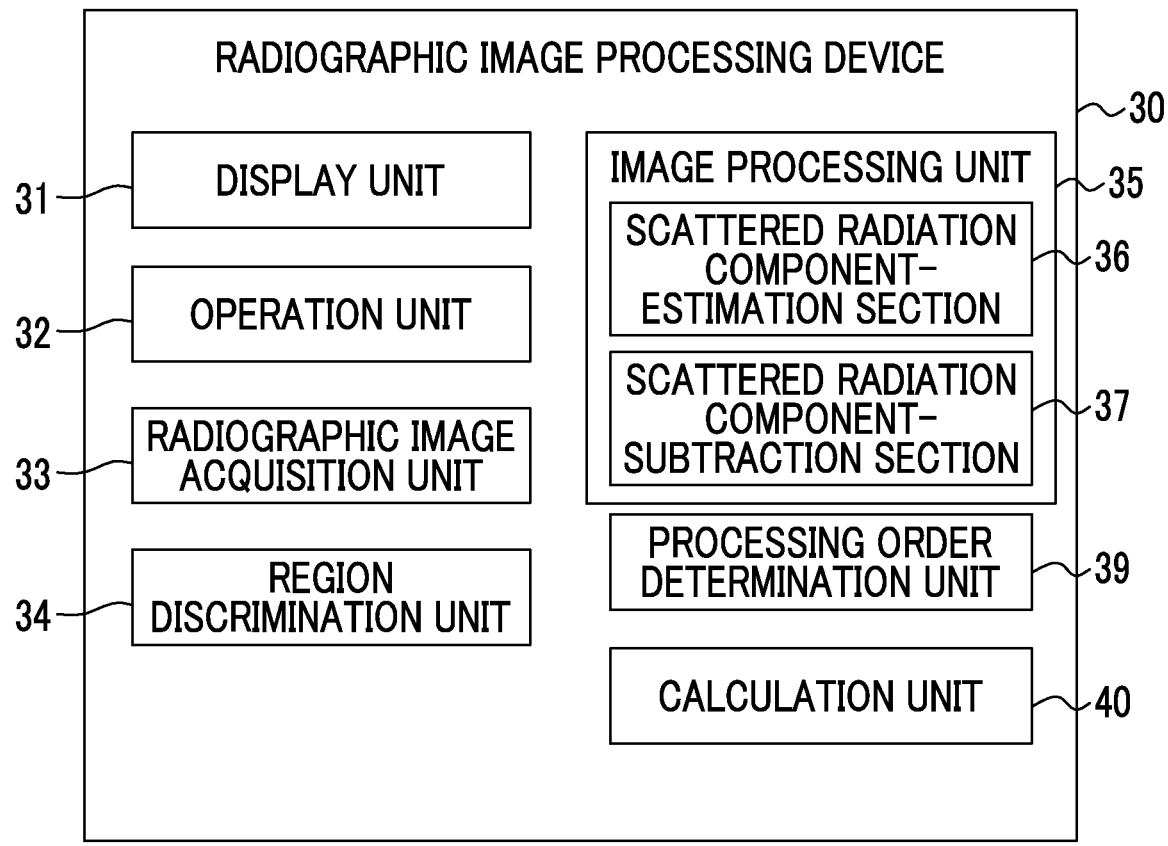
FIG. 2 is a block diagram showing the configuration of a radiographic image processing device.

As shown in FIG. 2, the radiographic image processing device 30 is a so-called computer and comprises a display unit 31, an operation unit 32, a radiographic image acquisition unit 33, a region discrimination unit 34, an image processing unit 35, a processing order determination unit 39, and a calculation unit 40.

The display unit 31 is a liquid crystal display or the like, and displays the taken radiographic images, images generated by the radiographic image processing device 30, and the like. The operation unit 32 is a keyboard and/or a pointing device, or the like that are used to operate the radiographic image processing device 30. The display unit 31 and the operation unit 32 can be formed of touch panels. The radiographic image processing device 30 is a device separate from the console 20 in this embodiment, but a part of the radiographic image processing device 30 or the entire radiographic image processing device 30 can be provided in the console 20. In this case, the display unit 21 and/or operation unit 22 of the console 20 can be used as the display unit 31 and/or the operation unit 32 of the radiographic image processing device 30. Further, the console 20 forms the radiographic image processing device 30 in a case where the entire radiographic image processing device 30 is provided in the console 20.

The radiographic image acquisition unit 33 acquires radiographic images that are taken from the subject Obj using the radiation Ra. The radiographic image acquisition unit 33 can acquire radiographic images from the console 20, RIS, HIS, PACS, or the like. In this embodiment, the radiographic image acquisition unit 33 directly acquires the radiographic images, which are taken by the radiographic imaging system 10, from the console 20. Further, the radiographic image acquisition unit 33 acquires the first radiographic image G1 output by the first radiation detector 15 and the second radiographic image G2 output by the second radiation detector 16. In a case where the radiographic image acquisition unit 33 acquires the radiographic images, the radiographic image acquisition unit 33 may acquire not only so-called original images (images not subjected to image processing and the like) but also the radiographic images subjected to various kinds of processing, such as processing for adjusting contrast and the like or other image processing.

The region discrimination unit 34 discriminates a plurality of regions using the radiographic images that are acquired by the radiographic image acquisition unit 33. Further, in a case where the radiographic image acquisition unit 33 acquires a plurality of radiographic images, the region discrimination unit 34 discriminates regions for every radiographic image or discriminates regions using at least one of the plurality of radiographic images. The "regions" discriminated by the region discrimination unit 34 means portions of the radiographic image that have specific characteristics in terms of positions, sizes, ranges, pixel values, or the like and can be distinguished from other portions due to the characteristics. For this reason, there is a case where some or all of the "regions" discriminated by the region discrimination unit 34 overlap other regions. Further, "discriminating" a region means recognizing (specifying or determining) the boundary (for example, a contour line or a boundary zone having a width) of a region, and includes recognizing the boundary of a specific region, thereby recognizing regions not belonging to the specific region. That is, the discrimination of a certain region using the region discrimination unit 34 is synonymous with the discrimination of regions positioned outside the discriminated region using the region discrimination unit 34.

There is a case where the region discrimination unit 34 discriminates only one region. Since boundaries and the like are not substantially present in a case where substantially the same subjects Obj appear in the entire radiographic image, the region discrimination unit 34 discriminates the entire radiographic image as one region. Further, "the radiographic images acquired by the radiographic image acquisition unit 33" to be used for region discrimination processing by the region discrimination unit 34 include the radiographic images that are acquired by the radiographic image acquisition unit 33 and are subjected to processing, such as image processing, by the radiographic image processing device 30, other radiographic image processing devices or the like, in addition to the radiographic images that are acquired by the radiographic image acquisition unit 33. That is, the region discrimination unit 34 can use the radiographic images acquired by the radiographic image acquisition unit 33 just it is, but can use radiographic images subjected to predetermined image processing or the like to allow the region discrimination unit 34, for example, to easily discriminate a region (to improve the accuracy of the discrimination of a region). Further, the region discrimination processing is performed according to pixel values, statistics (the maximum value and the like) showing the distribution of pixel values and the like, the shape (including the height of a peak and the like) of the appearance frequency histogram of pixel values, the recognition of a pattern, threshold value processing, recognition using a learned model, or the like.

Figure 3:
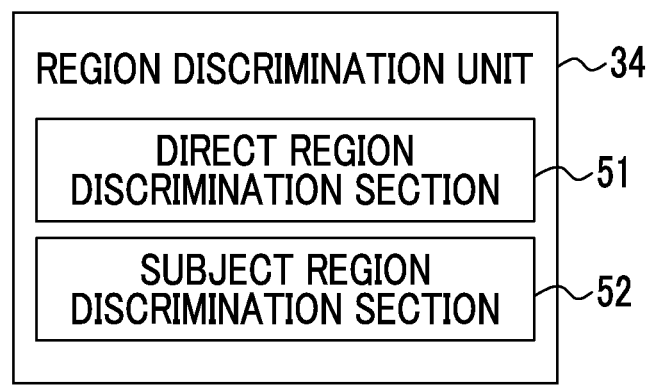
FIG. 3 is a block diagram of a region discrimination unit.

In this embodiment, the region discrimination unit 34 includes a direct region discrimination section 51 and a subject region discrimination section 52 as shown in FIG. 3 and performs region discrimination processing using the direct region discrimination section 51 and the subject region discrimination section 52. The direct region discrimination section 51 discriminates a region (hereinafter, referred to as a direct region) X1 of an input radiographic image where the radiation Ra directly reaches the radiation detector without being transmitted through the subject Obj (see FIG. 5). Further, the subject region discrimination section 52 discriminates a region (hereinafter, referred to as a subject region) X2 where the radiation Ra reaches the radiation detector through the subject Obj (see FIG. 5). That is, the region discrimination unit 34 discriminates the direct region X1 and the subject region X2 in this embodiment.

The image processing unit 35 generates a scattered radiation component-subtracted image where scattered radiation components have been subtracted. For this purpose, the image processing unit 35 includes a scattered radiation component-estimation section 36 and a scattered radiation component-subtraction section 37.

The scattered radiation component-estimation section 36 estimates the scattered radiation components of radiation of each region using scattered radiation component-estimation processing that varies for each region discriminated by the region discrimination unit 34. Accordingly, the scattered radiation component-estimation section 36 can perform a plurality of types of scattered radiation component-estimation processing. Further, in a case where the scattered radiation component-estimation section 36 performs scattered radiation component-estimation processing in a specific region, the scattered radiation component-estimation section 36 performs one type of scattered radiation component-estimation processing, which is suitable for the region to be subjected to processing, among the plurality of types of scattered radiation component-estimation processing. The scattered radiation component-estimation section 36 can perform another scattered radiation component-estimation processing while using the result of specific scattered radiation component-estimation processing as a parameter, or can combine a plurality of types of scattered radiation component-estimation processing to perform a plurality of pieces of scattered radiation component-estimation processing in one region. However, in this case, the plurality of types of scattered radiation component-estimation processing to be combined form one type of scattered radiation component-estimation processing that is separate from each scattered radiation component-estimation processing as a whole. The scattered radiation components of a specific region mean scattered radiation components generated from the radiation Ra radiated toward the specific region, and include components incident on other regions of the radiographic imaging panel 14 (the first radiation detector 15, or the like).

Figure 4:
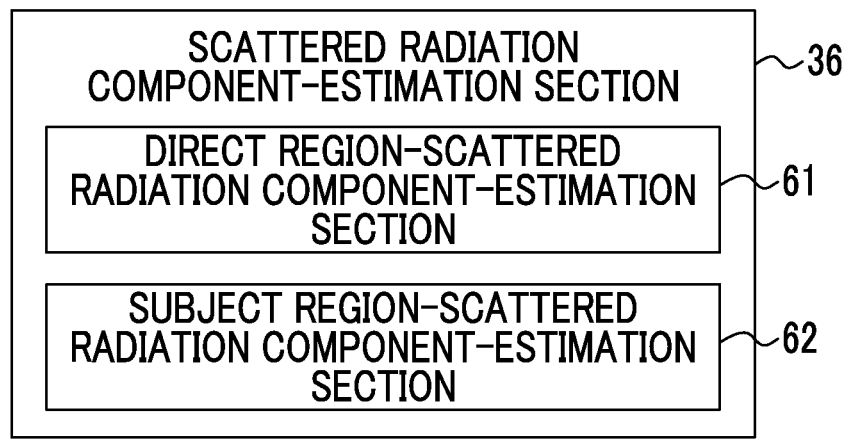
FIG. 4 is a block diagram of a scattered radiation component-estimation section.

In this embodiment, as shown in FIG. 4, the scattered radiation component-estimation section 36 includes a direct region-scattered radiation component-estimation section 61 and a subject region-scattered radiation component-estimation section 62 to cope with a case where the region discrimination unit 34 discriminates the direct region X1 and the subject region X2.

The direct region-scattered radiation component-estimation section 61 estimates scattered radiation components included in the direct region X1, which is discriminated by the region discrimination unit 34, by scattered radiation component-estimation processing for the direct region X1 (hereinafter, referred to as scattered radiation component-estimation processing for a direct region). The scattered radiation component-estimation processing for a direct region is scattered radiation component-estimation processing specialized to estimate the scattered radiation components of the direct region X1, and can estimate the scattered radiation components of the direct region X1 with a higher accuracy than scattered radiation component-estimation processing for the subject region X2. "The scattered radiation components of the direct region X1" means scattered radiation components generated from the radiation Ra radiated toward the direct region X1, and includes components incident on a region of the radiographic imaging panel 14 (the first radiation detector 15 or the like) outside the direct region X1.

Figure 5:
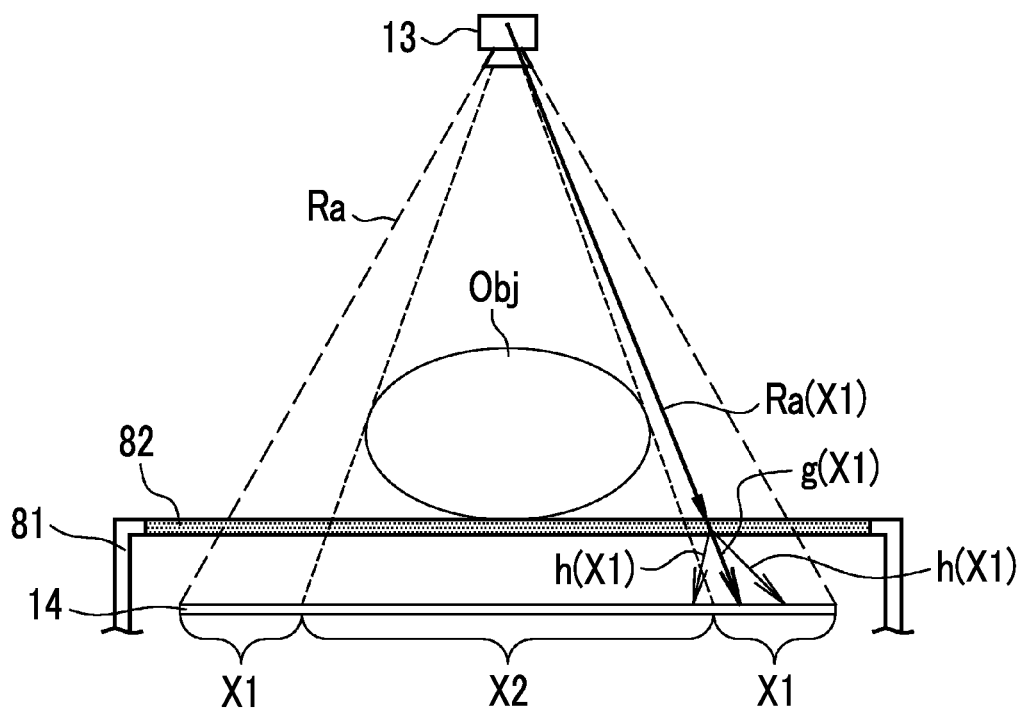
FIG. 5 is a diagram illustrating the region of a radiographic image and a scatterer.

For example, in a case where the subject Obj is placed on a bed 81 and is imaged as shown in FIG. 5, the radiation Ra reaches the direct region X1 through a top board 82 of the bed 81. Accordingly, for simplification, a scatterer for radiation Ra(X1) radiated toward the direct region X1 from the radiation source 13 is assumed as only the top board 82. In a case where the radiation Ra(X1) is incident on the top board 82, some components (so-called primary radiation components) g(X1) continue to go straight and reach the radiographic imaging panel 14 (the first radiation detector 15 or the like). On the other hand, the paths of other components are changed due to scattering caused by the top board 82, and the components form scattered radiation components h(X1) and reach the radiographic imaging panel 14. Accordingly, the distribution f(X1) of the radiation Ra(X1), which is radiated toward the direct region X1, on the radiographic imaging panel 14 is the sum of the primary radiation components g(X1) and the scattered radiation components h(X1). That is, "f(X1)=g(X1)+h(X1)" is satisfied.

Figure 6:
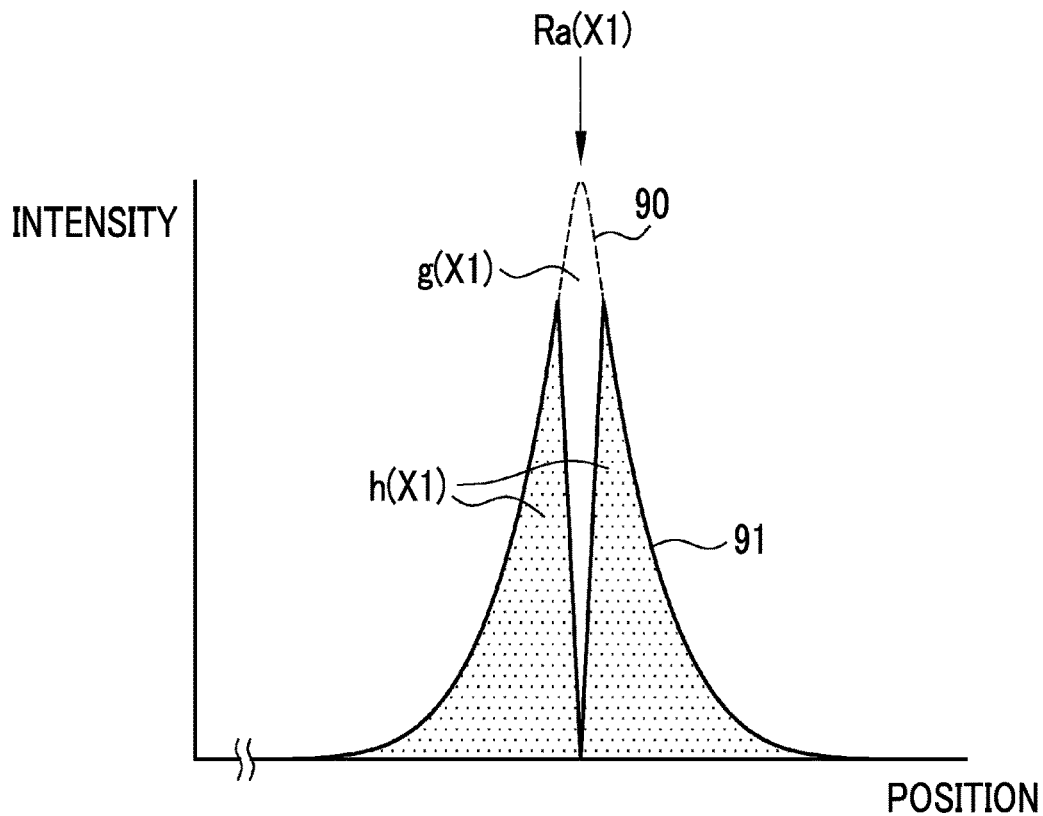
FIG. 6 is a graph showing a scattered radiation component distribution.

On the other hands, the distribution of the radiation Ra passing through any one point on the top board 82 can be approximated by a point spread function (PSF). A PSF is, for example, a Gaussian function. For this reason, as shown in FIG. 6, a portion, which excludes primary radiation components, of a PSF 90, which includes primary radiation components and scattered radiation components passing through any one point on the top board 82, is a distribution (hereinafter, referred to as a scattered radiation component distribution) 91 representing the diffusion of the scattered radiation components.

Further, since the energy and the like of the radiation Ra used for imaging and the material (density and the like) and thickness (mass) of the top board 82 as a scatterer are already known, the specific shape of the scattered radiation component distribution 91, such as the height of a peak and a half-width, are determined in advance. Accordingly, the direct region-scattered radiation component-estimation section 61 can estimate the scattered radiation components h(X1) of the direct region X1 with high accuracy by the deconvolution of the scattered radiation component distribution 91.

The subject region-scattered radiation component-estimation section 62 estimates scattered radiation components included in the subject region X2, which is discriminated by the region discrimination unit 34, by scattered radiation component-estimation processing for the subject region X2 (hereinafter, referred to as scattered radiation component-estimation processing for a subject region). The scattered radiation component-estimation processing for a subject region is scattered radiation component-estimation processing specialized to estimate the scattered radiation components of the subject region X2, and can estimate the scattered radiation components of the subject region X2 with a higher accuracy than the scattered radiation component-estimation processing for a direct region. "The scattered radiation components of the subject region X2" means scattered radiation components generated from the radiation Ra radiated toward the subject region X2, and includes components incident on a region of the radiographic imaging panel 14 (the first radiation detector 15 or the like) outside the subject region X2.

Figure 7:
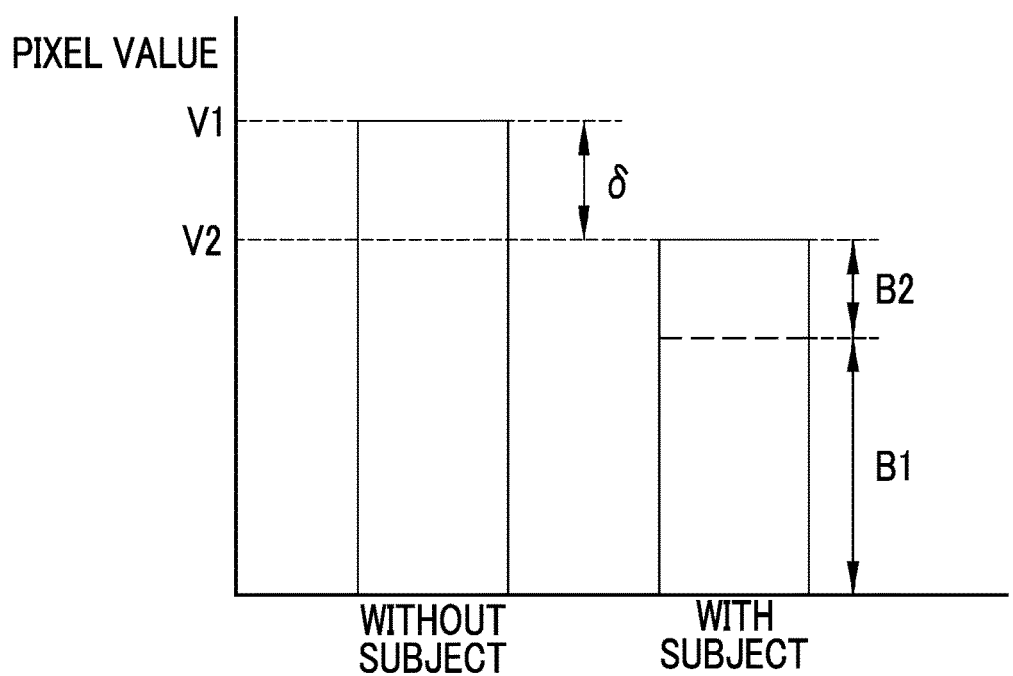
FIG. 7 is a diagram illustrating the configuration of the pixel values of a subject region.

For example, a main scatterer for radiation Ra(X2) generated radiated toward the subject region X2 from the radiation source 13 is the subject Obj. Further, as shown in FIG. 7, a pixel value V2 in a case where a subject Obj is present ("with subject") is smaller than a pixel value V1 in a case where the subject Obj is not present ("without subject"). Since this is caused by the absorption of the subject Obj or the like, a difference δ(=V1−V2) between the pixel values is related to the thickness of the subject Obj. Further, the pixel value V1 in a case where the subject Obj is not present can be known from the pixel values of the direct region X1, the pixel values of the direct region X1 where the scattered radiation components h(X1) have been subtracted, the experiments performed in advance, or the like. For this reason, the subject region-scattered radiation component-estimation section 62 can estimate the subject Obj from the pixel value V2 of the subject region X2 of the radiographic image.

Further, the pixel value V2 of the subject region X2 of the radiographic image is formed of a primary radiation component B1 and a scattered radiation component B2, and the quantity (magnitude) of the scattered radiation component B2 of these radiation components is related to the thickness of the subject Obj. For this reason, the subject region-scattered radiation component-estimation section 62 can estimate the scattered radiation component B2 at each pixel of the subject region X2 using the estimated thickness of the subject Obj. Accordingly, the subject region-scattered radiation component-estimation section 62 can estimate scattered radiation components h(X2), which is the distribution of the scattered radiation components B2 of the subject region X2, from the distribution of the pixel values in the subject region X2 with high accuracy.

The scattered radiation component-subtraction section 37 subtracts the scattered radiation components of each region, which is discriminated by the region discrimination unit 34, from the input radiographic image. For example, in a case where the radiographic image acquired by the radiographic image acquisition unit 33 and the scattered radiation components h(X1) of the direct region X1 are obtained, the scattered radiation component-subtraction section 37 generates a direct region-scattered radiation component-subtracted image by subtracting the scattered radiation components h(X1) of the direct region X1 from the radiographic image acquired by the radiographic image acquisition unit 33. Further, in a case where the direct region-scattered radiation component-subtracted image and the scattered radiation components h(X2) of the subject region X2 are obtained, the scattered radiation component-subtraction section 37 generates a subject region-scattered radiation component-subtracted image by subtracting the scattered radiation components h(X2) of the subject region X2 from the direct region-scattered radiation component-subtracted image. "Subtracting the scattered radiation components of each region" means subtracting scattered radiation components that are generated from the radiation Ra radiated toward a specific region. For this reason, a region where the scattered radiation component-subtraction section 37 subtracts scattered radiation components is not limited to the specific region. In a case where the scattered radiation components of the specific region reach the other region, the scattered radiation component-subtraction section 37 also subtracts scattered radiation components from the other region.

The image processing unit 35 uses the scattered radiation component-estimation section 36 and the scattered radiation component-subtraction section 37 to sequentially estimate and subtract the scattered radiation components of each region discriminated by the region discrimination unit 34.

As a result, the image processing unit 35 generates a scattered radiation component-subtracted image where scattered radiation components have been subtracted. In this embodiment, the image processing unit 35 estimates and subtracts the scattered radiation components h(X1) of the direct region X1 and then estimates and subtracts the scattered radiation components h(X2) of the subject region X2. For this reason, the subject region-scattered radiation component-subtracted image is a scattered radiation component-subtracted image that is finally output by the image processing unit 35.

The processing order determination unit 39 determines an order of regions in which the image processing unit 35 estimates and subtracts scattered radiation components. A processing order determined by the processing order determination unit 39 is an order in which a region where the number of types of scatterers scattering the radiation Ra is smaller is processed earlier. That is, the processing order determination unit 39 determines a processing order in which the processing of a simple system is performed earlier and the processing of a complex system is performed later. Generally, the accuracy of the estimation of the scattered radiation components of a region, which forms a simple system in which the number of the types of scatterers to be considered is small, is high. For this reason, in a case where the scattered radiation components of a region forming a complex system are estimated after the scattered radiation components of a region forming a simple system are estimated and subtracted, the scattered radiation components of a region forming a complex system can be estimated and subtracted in a clean state where the scattered radiation components of a region forming a simple system are estimated and subtracted with high accuracy. As a result, the accuracy of the estimation of the scattered radiation components of a region, which forms a complex system, is improved. This effect is significant near the boundaries of each region, that is, in a range where the scattered radiation components h(X1) and/or scattered radiation components h(X2) reach. Accordingly, since a range where the scattered radiation components h(X1) and/or scattered radiation components h(X2) reach in a case where radiographic imaging is performed without using a grid is larger than that in a case where radiographic imaging is performed using a grid, the above-mentioned effect is particularly significant in a case where radiographic imaging is performed without using a grid.

Since the scattered radiation components of the direct region X1 and the subject region X2 are estimated and subtracted in this embodiment, the processing order determination unit 39 determines an order in which the scattered radiation components h(X1) of the direct region X1 are estimated and subtracted first and the scattered radiation components h(X2) of the subject region X2 are then estimated and subtracted. A scatterer is only the top board 82 in the direct region X1, but there are two scatterers, that is, the subject Obj and the top board 82 in the subject region X2. For this reason, the direct region X1 corresponds to a relatively simple system and the accuracy of the estimation of the scattered radiation components h(X1) of the direct region X1 is higher, and the subject region X2 corresponds to a relatively complex system and the accuracy of the estimation of the scattered radiation components h(X1) of the subject region X2 is lower. That is, in a case where the region discrimination unit 34 discriminates the direct region X1 and the subject region X2, according to the above-mentioned determination of the processing order determination unit 39, the image processing unit 35 generates the direct region-scattered radiation component-subtracted image by subtracting the scattered radiation components h(X1) of the direct region X1 from the radiographic image acquired by the radiographic image acquisition unit 33 and generates the subject region-scattered radiation component-subtracted image by further subtracting the scattered radiation components h(X2) of the subject region X2 from the direct region-scattered radiation component-subtracted image. Then, the image processing unit 35 outputs the subject region-scattered radiation component-subtracted image as a final scattered radiation component-subtracted image. This scattered radiation component-subtracted image is a radiographic image of which the scattered radiation components of each region are reduced by the subtraction of both the scattered radiation components h(X1) of the direct region X1 and the scattered radiation components h(X2) of the subject region X2 as described above.

The processing order determination unit 39 can flexibly determine the processing order according to the types and/or the number of the regions discriminated by the region discrimination unit 34. Further, in a case where the types of regions that can be discriminated by the region discrimination unit 34 are determined in advance and systems corresponding to the respective regions are already known (scatterers to be considered are already known), the processing order determination unit 39 can determine the processing order in advance. In this case, in a case where the region discrimination unit 34 does not discriminate a specific region (the specific region is not present), the processing order determination unit 39 skips processing for estimating and subtracting scattered radiation components of a type of region, which is not present as a result of discrimination processing, from the processing order determined in advance. Further, the processing order determination unit 39 can accept the designation of a processing order according to manual setting inputs and the like of a radiological technician, a doctor, or the like. In this embodiment, the processing order determination unit 39 determines a processing order in advance.

The calculation unit 40 makes a calculation using the scattered radiation component-subtracted image that is output by the image processing unit 35. For example, the calculation unit 40 generates a so-called subtraction image using a first scattered radiation component-subtracted image where the scattered radiation components of each region have been sequentially subtracted from the first radiographic image G1 obtained from the first radiation detector 15 and a second scattered radiation component-subtracted image where the scattered radiation components of each region have been sequentially subtracted from the second radiographic image G2 obtained from the second radiation detector 16. The subtraction image is a highlight image that highlights specific structures included in the subject Obj, and is generated in a case where subtraction processing of a radiographic image is performed by multiplying each pixel or each region where a recognized structure is present by the attenuation coefficient $\mu$ of the structure. In this case, each of the first scattered radiation component-subtracted image and the second scattered radiation component-subtracted image used in the subtraction processing is a radiographic image where the scattered radiation components of each region have been subtracted with high accuracy, and errors caused by the scattered radiation components is particularly reduced. As a result, errors caused by the scattered radiation components are small even after the subtraction processing. Accordingly, specific structures can be more accurately highlighted as compared to a case where the first and second scattered radiation component-subtracted images where the scattered radiation components of each region have been sequentially subtracted are not used. The calculation unit 40 can make a calculation other than the subtraction processing using a scattered radiation component-subtracted image where the scattered radiation components of each region have been sequentially subtracted. For example, the calculation unit 40 can obtain numerical values, such as bone mineral content, according to the composition of the subject Obj and the like using a scattered radiation component-subtracted image where the scattered radiation components of each region have been sequentially subtracted. In this case, since a scattered radiation component-subtracted image where the scattered radiation components of each region have been sequentially subtracted is used, pixel values where scattered radiation components have been reduced with high accuracy and the like can be used for calculation. Accordingly, bone mineral content and the like can be more accurately calculated than that in a case where the pixel values are not used.

Figure 8:
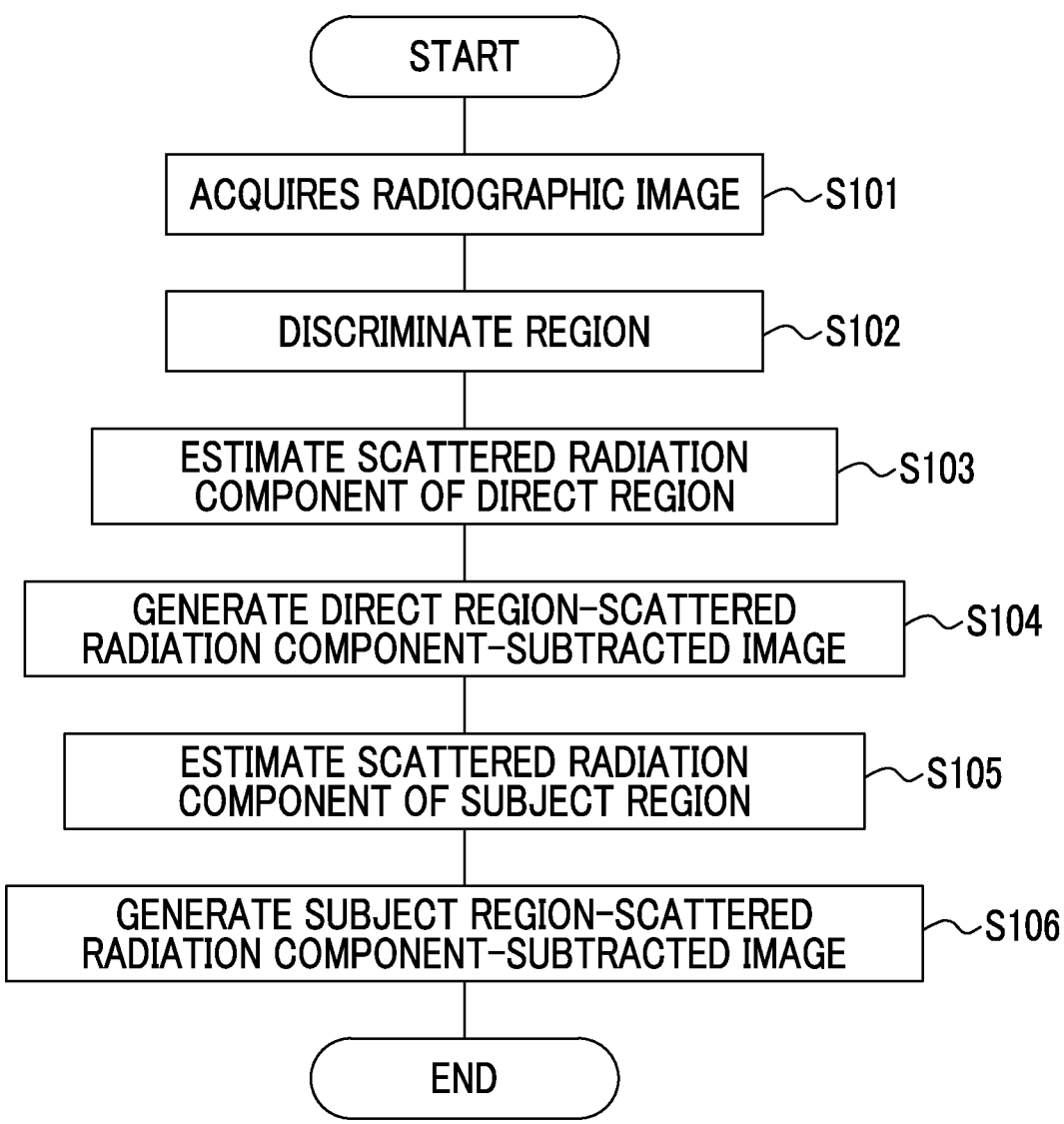
FIG. 8 is a flowchart showing an operation for estimating and subtracting scattered radiation components (radiographic image processing method).

An operation for estimating and subtracting scattered radiation components (radiographic image processing method) performed by the radiographic image processing device 30 having the above-mentioned configuration will be described below. As shown in FIG. 8, the radiographic image acquisition unit 33 acquires radiographic images that are taken from the subject Obj using the radiation Ra (Step S101 (radiographic image acquisition step)). In this embodiment, the radiographic image acquisition unit 33 acquires the first radiographic image G1 taken using the first radiation detector 15 and the second radiographic image G2 taken using the second radiation detector 16.

Figure 9:
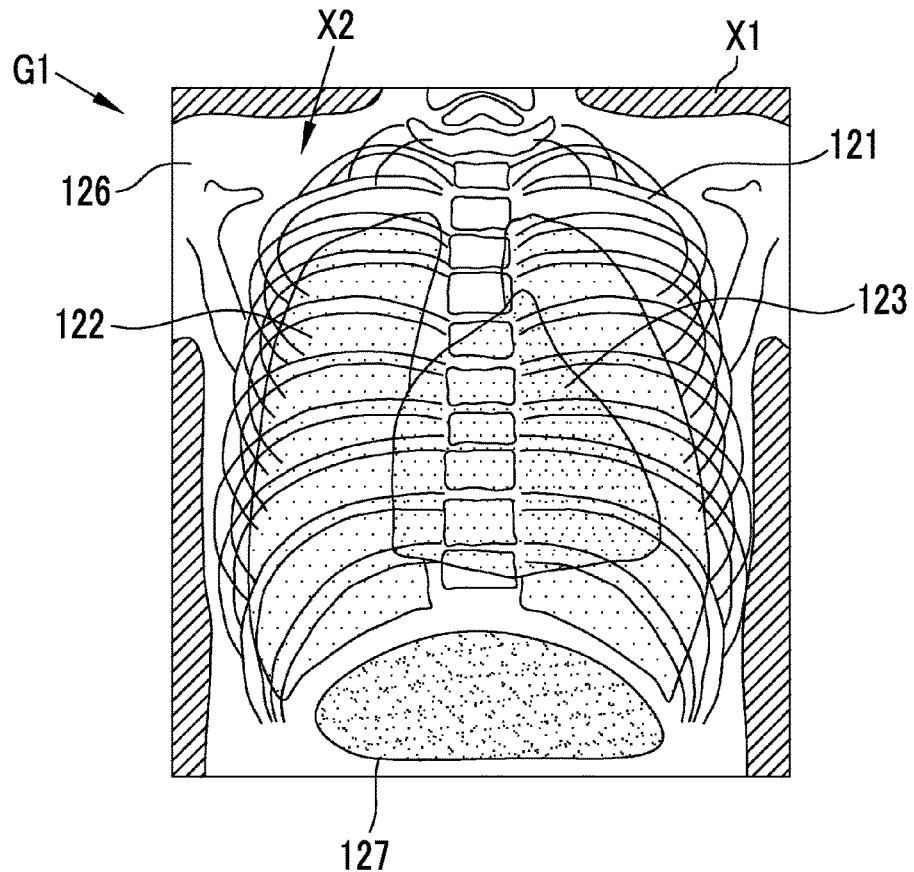
FIG. 9 is a first radiographic image in a case where the chest of a human body is imaged.

For example, in a case where the subject Obj is a human and the chest of the human is a portion to be imaged, a bony part 121, such as the ribs, the lungs 122, the heart 123, muscle 126 of the shoulders, upper arms, or the like, the fat 127, and the like appear in the first radiographic image G1 as shown in FIG. 9. Further, the chest, the respective tissues near the chest, and the like appear to overlap. That is, there is a case where some or all of the images (shades) of these tissues and the like overlap the images of other tissues. All these images of the subject Obj are the subject region X2. Furthermore, the first radiographic image G1 includes the direct region X1. The second radiographic image G2 is also the same as the first radiographic image, but the first radiographic image G1 and the second radiographic image G2 are substantially different from each other in the energy of the radiation Ra used for imaging. Accordingly, in a case where the images of the respective tissues of the first radiographic image G1 are compared with the images of the respective tissues of the second radiographic image G2, the magnitudes of the pixel values of the respective tissues of corresponding portions are also different from each other. As a result, the first radiographic image G1 and the second radiographic image G2 are different from each other in the relative brightness and/or contrast, and the like of the respective tissues.

In a case where the radiographic image acquisition unit 33 acquires the first radiographic image G1 and the second radiographic image G2, the region discrimination unit 34 discriminates specific regions from the first radiographic image G1 and/or the second radiographic image G2 (Step S102 (region discrimination step)). In this embodiment, the region discrimination unit 34 discriminates a region using the first radiographic image G1 in a case where scattered radiation components are estimated and subtracted from the first radiographic image G1, and discriminates a region using the second radiographic image G2 in a case where scattered radiation components are estimated and subtracted from the second radiographic image G2. Further, the region discrimination unit 34 discriminates the direct region X1 using the direct region discrimination section 51, and discriminates the subject region X2 using the subject region discrimination section 52.

In a case where the discrimination of the regions is completed, the image processing unit 35 sequentially estimates and subtracts the scattered radiation components of each region according to the processing order determined by the processing order determination unit 39 (Steps S103 to S106). In this embodiment, the image processing unit 35 estimates and subtracts the scattered radiation components h(X1) of the direct region X1 first (Steps S103 to S104). That is, the direct region-scattered radiation component-estimation section 61 estimates the scattered radiation components h(X1) of the direct region X1 (Step S103 (scattered radiation component-estimation step)). After that, the image processing unit 35 generates a direct region-scattered radiation component-subtracted image by subtracting the scattered radiation components h(X1) of the direct region X1 from the original radiographic image (the first radiographic image G1 or the second radiographic image G2) using the scattered radiation component-subtraction section 37 (Step S104).

Then, the image processing unit 35 estimates and subtracts the scattered radiation components h(X2) of the subject region X2 (Steps 5105 to S106). That is, the subject region-scattered radiation component-estimation section 62 estimates the scattered radiation components h(X2) of the subject region X2 (Step 5105 (scattered radiation component-estimation step)). After that, the image processing unit 35 generates a subject region-scattered radiation component-subtracted image by subtracting the scattered radiation components h(X2) of the subject region X2 from the direct region-scattered radiation component-subtracted image using the scattered radiation component-subtraction section 37 (Step S106).

As a result, the image processing unit 35 outputs the subject region-scattered radiation component-subtracted image where the scattered radiation components h(X1) of the direct region X1 and the scattered radiation components h(X2) of the subject region X2 have been subtracted from the original radiographic image as a "scattered radiation component-subtracted image".

The image processing unit 35 sequentially estimates and subtracts the scattered radiation components of each region, which is discriminated by the region discrimination unit 34, using the scattered radiation component-estimation section 36 and the scattered radiation component-subtraction section 37, so that the radiographic image processing device 30 generates a scattered radiation component-subtracted image where scattered radiation components have been subtracted as described above. For this reason, the radiographic image processing device 30 can reduce the scattered radiation components of the radiographic image with high accuracy. For example, in a case where scattered radiation components are to be subtracted in the related art by image processing, scattered radiation components are estimated and subtracted by an optimum method as a whole without the discrimination of regions. However, since the region discrimination unit 34 discriminates regions and different scattered radiation component-estimation processing is used for each discriminated region, the radiographic image processing device 30 can estimate and subtract scattered radiation components by an optimum method for each region. As a result, the radiographic image processing device 30 can estimate and subtract scattered radiation components with higher accuracy than the image processing in the related art.

Further, since the direct region X1 is a portion where the image of the subject Obj is not present in a radiographic image processing device in the related art and the like, the scattered radiation components h(X1) of the direct region X1 are not estimated and subtracted while focusing attention on the direct region X1. However, while focusing attention on the direct region X1 in the first embodiment, the estimation and subtraction of the scattered radiation components h(X1) of the direct region X1 are performed prior to the estimation and subtraction of the scattered radiation components h(X2) of the subject region X2. As a result, the accuracy of the estimation and subtraction of the scattered radiation components h(X2) of the subject region X2 to be performed later can be improved. Since the direct region X1 corresponds to a relatively simple system and the scattered radiation components h(X1) of the direct region X1 can be estimated and subtracted with high accuracy, the scattered radiation components h(X2) of the subject region X2 can be estimated and subtracted on the basis of an image state that is cleaner than that in the related art.

Second Embodiment

In the first embodiment, the direct region X1 and the subject region X2 are discriminated and the scattered radiation components of these two regions are estimated and subtracted. However, the radiographic image processing device 30 can discriminate regions other than the direct region X1 and the subject region X2 and can estimate and subtract the scattered radiation components of each of the regions.

Figure 10:
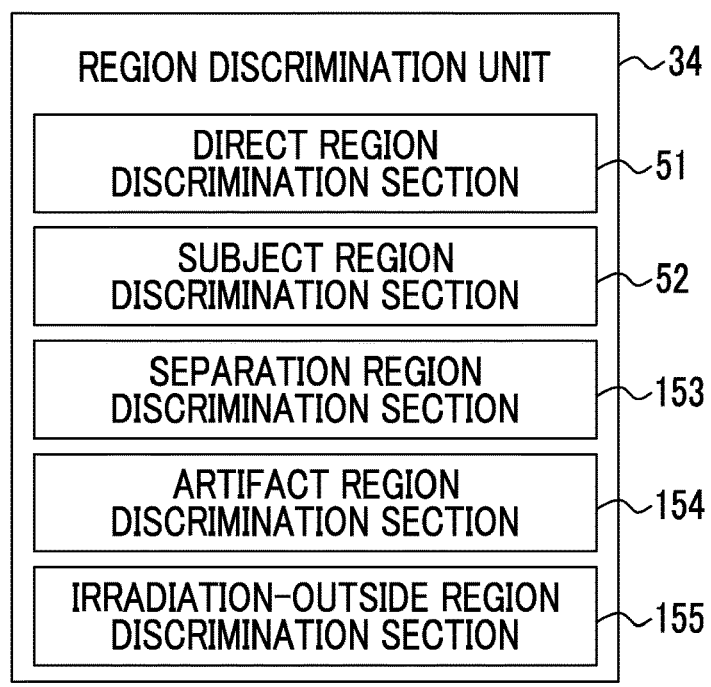
FIG. 10 is a block diagram showing the configuration of a region discrimination unit of a second embodiment.

For example, as shown in FIG. 10, the region discrimination unit 34 can be provided with a separation region discrimination section 153, an artifact region discrimination section 154, an irradiation-outside region discrimination section 155, and the like in addition to the direct region discrimination section 51 and the subject region discrimination section 52.

Figure 11:
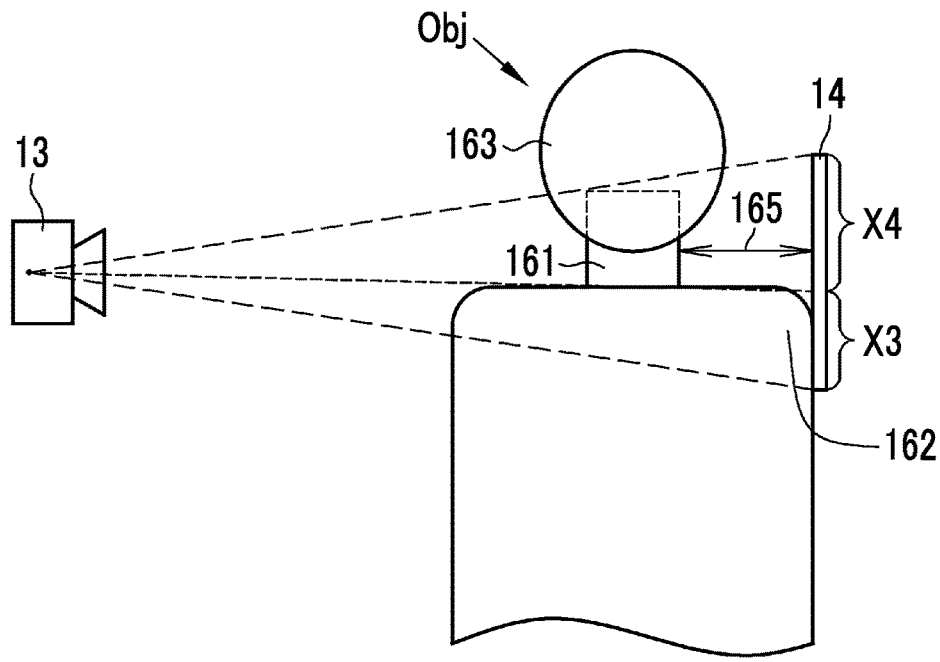
FIG. 11 is a diagram illustrating a separation region.

The separation region discrimination section 153 discriminates a contact region X3 where the subject Obj is in contact with the radiographic imaging panel 14 serving as a radiation detector for taking a radiographic image, and a separation region X4 where the subject Obj is separated from the radiographic imaging panel 14 serving as the radiation detector. For example, in a case where a neck 161 of the subject Obj is imaged from the side (shoulder 162 side) of the subject Obj, the neck 161 and a head 163 are separated from the radiographic imaging panel 14 and an air gap 165 is formed as shown in FIG. 11 since the shoulder 162 is in contact with the radiographic imaging panel 14. For this reason, the separation region discrimination section 153 discriminates, a region where the shoulder 162 or the like is in contact with the radiographic imaging panel 14 as the contact region X3 and discriminates a region where the neck 161 and the head 163 of the subject Obj appear as the separation region X4.

The artifact region discrimination section 154 discriminates an artifact region where an artifact mounted on the subject Obj or included in the subject Obj is present. The artifact mounted on the subject Obj is a radiation protector or the like. The artifact included in the subject Obj is a bolt inserted into the subject Obj, a contrast medium injected into the subject Obj, and the like.

The irradiation-outside region discrimination section 155 discriminates a region (hereinafter, referred to as an irradiation-outside region) outside a region irradiated with radiation Ra. The irradiation-outside region is a region on which the radiation Ra is not directly incident. There is a case where the irradiation-outside region is formed due to a relative positional relationship between the irradiation range of the radiation Ra, which is determined by a collimator (included in the radiation source 13), and the radiographic imaging panel 14.

Figure 12:
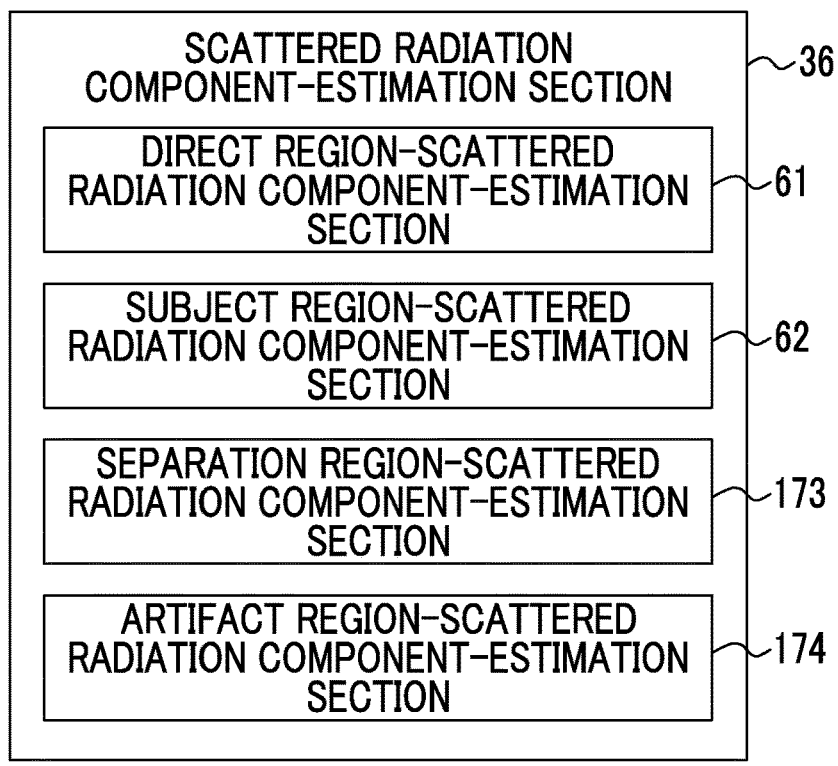
FIG. 12 is a block diagram showing the configuration of a scattered radiation component-estimation section of a second embodiment.

In a case where the region discrimination unit 34 discriminates regions other than the direct region X1 and the subject region X2 as described above, it is preferable that the region discrimination unit 34 is separately provided with a scattered radiation component-estimation processing section that estimates scattered radiation components of a region on which at least primary radiation of the radiation Ra is incident among the regions. For example, it is preferable that the scattered radiation component-estimation section 36 is provided with a separation region-scattered radiation component-estimation section 173 and an artifact region-scattered radiation component-estimation section 174 in addition to the direct region-scattered radiation component-estimation section 61 and the subject region-scattered radiation component-estimation section 62 as shown in FIG. 12.

The separation region-scattered radiation component-estimation section 173 estimates scattered radiation components h(X4) of the separation region X4 using scattered radiation component-estimation processing for the separation region X4. The scattered radiation components h(X4) of the separation region X4 can be estimated using the thickness of the subject Obj as in the case of the subject region X2, but the separation region-scattered radiation component-estimation section 173 further considers the presence of the air gap 165. The reason for this is that scattered radiation components are reduced depending on the width (thickness) of the air gap 165 in a case where the air gap 165 is present. The air gap 165 can be calculated from, for example, source to image distance (SID) and source to object distance (SOD), which are already known at the time of imaging, and the thickness of the subject Obj to be estimated. That is, a value that is obtained by subtracting SOD and the thickness of the subject Obj from SID is the width of the air gap 165.

The separation region X4 is a part of the subject region X2. For this reason, in a case where the separation region discrimination section 153 discriminates the separation region X4 (particularly, in a case where the separation region X4 is present), the subject region discrimination section 52 excludes the separation region X4 from the subject region X2. Then, the processing order determination unit 39 determines a processing order in which processing for estimating and subtracting the scattered radiation components h(X2) of the subject region X2 is performed prior to processing for estimating and subtracting the scattered radiation components h(X4) of the separation region X4. The reason for this is that the configuration of a scatterer of a system corresponding to the separation region X4 is complex since the air gap 165 is present. Accordingly, in a case where the direct region X1, the subject region X2 (excluding the separation region X4), and the separation region X4 are present, the order of the processing for estimating and subtracting scattered radiation components is the order of the direct region X1, the subject region X2 (excluding the separation region X4), and the separation region X4. The separation region X4 is discriminated in this way, the subject region X2 where the subject Obj is in contact with the radiographic imaging panel 14 serving as the radiation detector is distinguished from the separation region X4, and scattered radiation component-estimation processing suitable for each of the regions is performed, so that the accuracy of the estimation of the scattered radiation components h(X4) of the separation region X4 is improved. Further, since the separation region X4 having different scattering characteristics and the like is excluded from the subject region X2 in comparison with a case where the separation region X4 is not considered (the separation region X4 is considered as the same region as the subject region X2), processing for estimating the scattered radiation components h(X2) of the more uniform subject region X2 can be performed. Accordingly, the accuracy of the estimation of the scattered radiation components h(X2) of the subject region X2 is also improved. As a result, the accuracy of various kinds of calculation for the subject region X2 and the separation region X4 is also improved.

The artifact region-scattered radiation component-estimation section 174 estimates scattered radiation components of the artifact region using scattered radiation component-estimation processing for an artifact region. A case where the artifact region-scattered radiation component-estimation section 174 estimates scattered radiation components is a case where an artifact present in the artifact region transmits at least a part of the radiation Ra. In this case, the scattering of the radiation Ra caused by the artifact needs to be considered.

The artifact region is included in the subject region X2 in most cases. For this reason, the subject region discrimination section 52 excludes the artifact region from the subject region X2. Then, the processing order determination unit 39 determines a processing order in which processing for estimating and subtracting the scattered radiation components h(X2) of the subject region X2 is performed prior to processing for estimating and subtracting the scattered radiation components of the artifact region. The reason for this is that the configuration of a scatterer of a system corresponding to the artifact region is complex since the artifact is present. Accordingly, in a case where the direct region X1, the subject region X2 (excluding the artifact region), and the artifact region are present, the order of the processing for estimating and subtracting scattered radiation components is the order of the direct region X1, the subject region X2 (excluding the artifact region), and the artifact region. The artifact region is discriminated in this way, the subject region X2 where the subject Obj is in contact with the radiographic imaging panel 14 serving as the radiation detector is distinguished from the artifact region, and scattered radiation component-estimation processing suitable for each of the regions is performed, so that the accuracy of the estimation of the scattered radiation components of the artifact region is improved. Further, since the artifact region having different scattering characteristics and the like is excluded from the subject region X2 in comparison with a case where the artifact region is not considered (the artifact region is considered as the same region as the subject region X2), processing for estimating the scattered radiation components h(X2) of the more uniform subject region X2 can be performed. Accordingly, the accuracy of the estimation of the scattered radiation components h(X2) of the subject region X2 is also improved. As a result, the accuracy of various kinds of calculation for the subject region X2 and the artifact region is also improved.

Since scattered radiation components are not generated in a case where the artifact present in the artifact region is an object blocking the radiation Ra, the artifact region-scattered radiation component-estimation section 174 does not estimate the scattered radiation components of the artifact region. However, the subject region discrimination section 52 excludes the artifact region from the subject region X2 of which the scattered radiation components h(X2) are estimated. The reason for this is to improve the accuracy of the estimation of the scattered radiation components h(X2) of the subject region X2.

Since scattered radiation components are not generated in the irradiation-outside region, scattered radiation component-estimation processing is not performed. However, the irradiation-outside region is excluded from each region of which scattered radiation components are estimated. For example, the irradiation-outside region is not included in the direct region X1. The reason for this is to improve the accuracy of the estimation of scattered radiation components of other regions by excluding the irradiation-outside region.

Third Embodiment

The subject region discrimination section 52 discriminates the entire image of the subject Obj as the subject region X2 in the first embodiment, the second embodiment, modification examples thereof, and the like, but the subject region discrimination section 52 can discriminate the regions of the radiographic image for one component or a plurality of components of the subject Obj.

Figure 13:
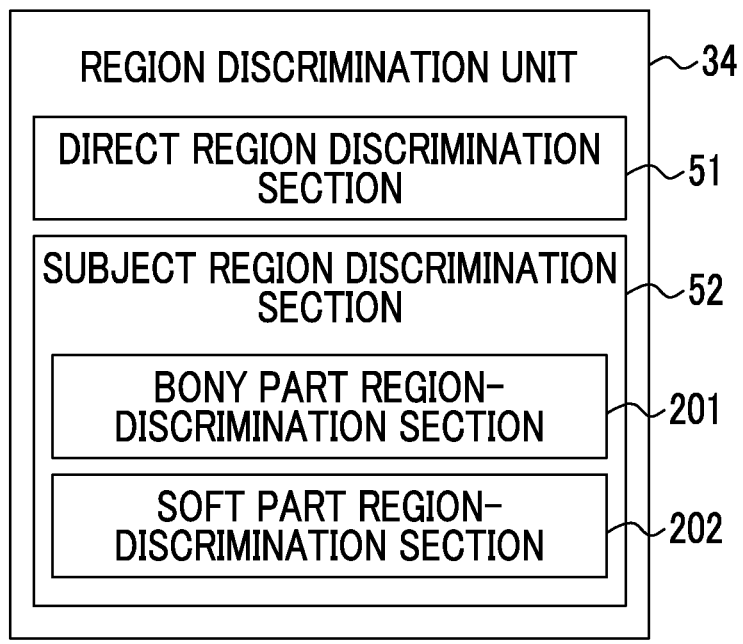
FIG. 13 is a block diagram showing the configuration of a region discrimination unit of a third embodiment.

For example, the subject region discrimination section 52 can discriminate a bony part region where bony parts of the subject Obj appear and a soft part region where soft part tissues appear while distinguishing the bony part region from the soft part region. In this case, as shown in FIG. 13, the region discrimination unit 34 is provided with a bony part region-discrimination section 201 and a soft part region-discrimination section 202 instead of the subject region discrimination section 52 or in addition to the subject region discrimination section 52. The bony part region-discrimination section 201 discriminates a bony part region of the subject region X2 of the first embodiment and the like. For example, the bony part region-discrimination section 201 discriminates the bony part 121, such as the ribs, as the bony part region in the first radiographic image G1 (see FIG. 9). The soft part region-discrimination section 202 discriminates a soft part region of the subject region X2 of the first embodiment and the like. For example, the soft part region-discrimination section 202 discriminates portions that are all soft part tissues, such as the lungs 122, the heart 123, muscle 126 of the shoulders, upper arms, or the like, and the fat 127, and exclude the bony part 121, such as the ribs, as a soft part region in the first radiographic image G1 (see FIG. 9). That is, all of the bony part region and the soft part region form the subject region X2 of the first embodiment and the like.

Figure 14:
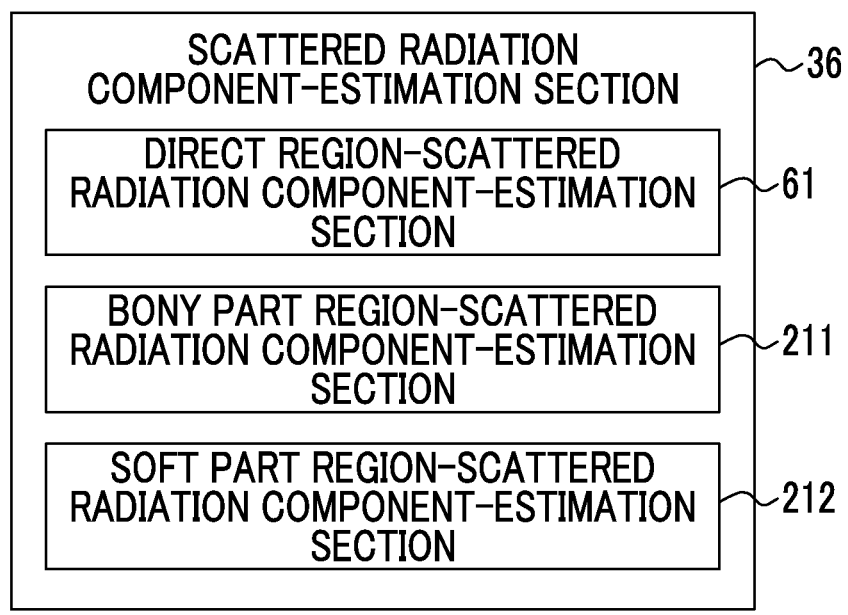
FIG. 14 is a block diagram showing the configuration of a scattered radiation component-estimation section of a third embodiment.
Figure 15:
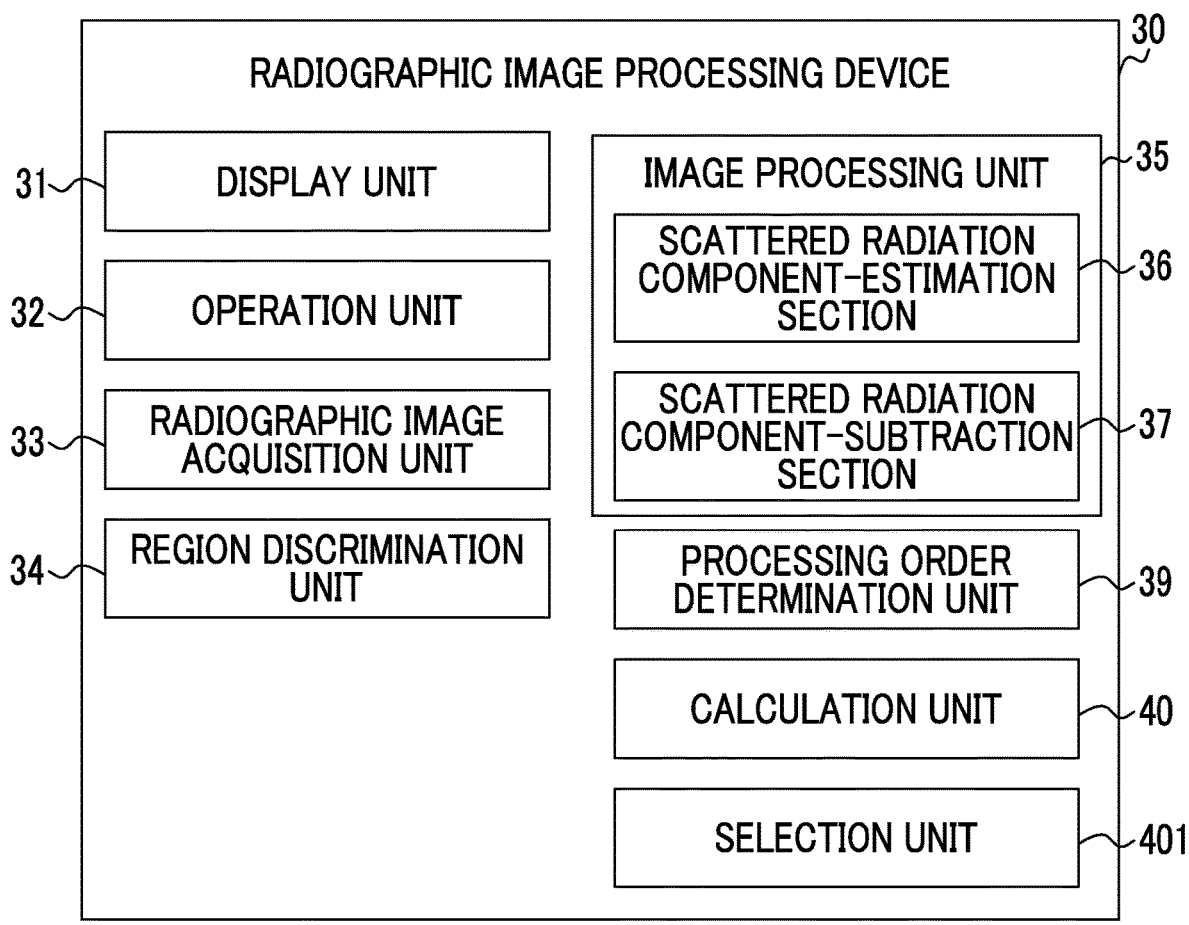
FIG. 15 is a block diagram of a radiographic image processing device of a fourth embodiment.

Further, as shown in FIG. 14, the scattered radiation component-estimation section 36 is provided with a bony part region-scattered radiation component-estimation section 211 and a soft part region-scattered radiation component-estimation section 212 that are divided from the subject region-scattered radiation component-estimation section 62. The bony part region-scattered radiation component-estimation section 211 estimates scattered radiation components of the bony part region using scattered radiation component-estimation processing for the bony part region. Further, the soft part region-scattered radiation component-estimation section 212 estimates scattered radiation components of the soft part region using scattered radiation component-estimation processing for the soft part region.

In a case where the subject region discrimination section 52 and the scattered radiation component-estimation section 36 are to be formed, the processing order determination unit 39 can determine a processing order in which processing for estimating and subtracting the scattered radiation components of the bony part region is performed prior to processing for estimating and subtracting the scattered radiation components of the soft part region, and can conversely determine a processing order in which processing for estimating and subtracting the scattered radiation components of the soft part region is performed prior to processing for estimating and subtracting the scattered radiation components of the bony part region. The bony part region is a region where the bony part 121 and the like and other soft part tissues overlap, and the soft part region is a region where a plurality of types of soft part tissues (the lungs 122, the heart 123, the muscle 126, the fat 127, and the like) overlap. Accordingly, the complexity of systems corresponding to these regions is changed depending on the setting the like of levels where these components of the subject Obj are considered as scatterers.

In a case where a difference between the soft part tissues as a scatterer for the radiation Ra is not considered, the bony part region forms a complex system that includes more scatterers than the soft part region since the bony part 121 is present in the bony part region. For this reason, in a case where a difference between the soft part tissues as a scatterer for the radiation Ra is not considered, a processing order in which processing for estimating and subtracting the scattered radiation components of the soft part region is performed prior to processing for estimating and subtracting the scattered radiation components of the bony part region is preferable. In a case where the direct region X1 is present in the radiographic image and the processing order is determined, the image processing unit 35 subtracts the scattered radiation components of the soft part region from the direct region-scattered radiation component-subtracted image and further subtracts the scattered radiation components of the bony part region from the direct region-scattered radiation component-subtracted image from which the scattered radiation components of the soft part region have been subtracted.

Since the bony part 121 is a characteristic component absorbing relatively much radiation Ra, an influence of the overlapping soft part tissues on the bony part 121 is relatively small. For this reason, there is a case where only the bony part 121 can be substantially treated as a scatterer for the radiation Ra in the estimation of the scattered radiation components of the bony part region. In this case, since a system corresponding to the bony part region forms a system that is simple substantially at the same level as the soft part region or is simpler than the soft part region, the accuracy of the estimation of the scattered radiation components of the bony part region is likely to be relatively high. Accordingly, it is preferable that a processing order in which processing for estimating and subtracting the scattered radiation components of the bony part region is performed prior to processing for estimating and subtracting the scattered radiation components of the soft part region is determined. In a case where the direct region X1 is present in the radiographic image and the processing order is determined, the image processing unit 35 subtracts the scattered radiation components of the bony part region from the direct region-scattered radiation component-subtracted image and further subtracts the scattered radiation components of the soft part region from the direct region-scattered radiation component-subtracted image from which the scattered radiation components of the bony part region have been subtracted.

In a case where the subject region X2 is further subdivided into a plurality of regions and the plurality of regions are discriminated and the scattered radiation components of each subdivided region are estimated using scattered radiation component-estimation processing for each subdivided region as described above, the accuracy of the estimation of the scattered radiation components of the subject region X2 is improved. That is, since the scattered radiation components of each of the bony part region and the soft part region are estimated, the accuracy of the estimation of the scattered radiation component of each of the bony part region and the soft part region is improved. The reason for this is that scattered radiation component-estimation processing having higher accuracy is performed since the regions having different scattering characteristics are excluded. As a result, the accuracy of various kinds of calculation for the subject region X2 is also improved.

The region discrimination unit 34 can further divide the soft part region into a plurality of regions according to composition and can discriminate the divided regions. For example, among the components of the subject Obj, the soft part tissues are distinguished according to the composition of the lungs 122, the heart 123, the muscle 126, the fat 127, and the like and regions can be discriminated. For example, as in the third embodiment, the soft part region-discrimination section 202 can be subdivided into a lung region-discrimination section, a heart region-discrimination section, a muscle region-discrimination section, a fat region-discrimination section, and the like, and the scattered radiation component-estimation section 36 can be provided with scattered radiation component-estimation sections corresponding to these regions. In this case, the scattered radiation components of each region having composition can be accurately estimated using scattered radiation component-estimation processing each region having composition.

Fourth Embodiment

The regions discriminated by the region discrimination unit 34 and the scattered radiation component-estimation processing for the respective regions are associated with each other in the first embodiment, the second embodiment, the third embodiment, and modification examples thereof, but it is preferable that any scattered radiation component-estimation processing can be selected for each of the regions discriminated by the region discrimination unit 34 from a plurality of pieces of scattered radiation component-estimation processing. The selection of the scattered radiation component-estimation processing is effective in, for example, a case where the region discrimination unit 34 is formed of a learned model (so-called artificial intelligence (AI)) and discriminates regions but it is not discriminated that the region is which region (whether the region is the direct region X1 or the subject region X2). The reason for this is that scattered radiation components can be exactly estimated since appropriate scattered radiation component-estimation processing can be performed for the region discriminated by the region discrimination unit 34.

For example, in a case where any scattered radiation component-estimation processing can be selected for each of the regions discriminated by the region discrimination unit 34 from a plurality of pieces of scattered radiation component-estimation processing, the radiographic image processing device 30 is provided with a selection unit 401. The selection unit 401 selects scattered radiation component-estimation processing for each of the regions discriminated by the region discrimination unit 34. The selection unit 401 can automatically select scattered radiation component-estimation processing to be applied to each region using the position, the size, the shape, and/or the density of each region. In this case, since the radiographic image processing device 30 automatically selects scattered radiation component-estimation processing to be applied to each region, convenience is good. Further, the selection unit 401 can display a graphical user interface (GUI) on, for example, the display unit 31 and accept the selection of scattered radiation component-estimation processing to be applied to each region. In this case, since a radiological technician, a doctor, or the like can manually select scattered radiation component-estimation processing to be applied to each region, correct scattered radiation component-estimation processing can be selected according to the intention and decision of a radiological technician, a doctor, or the like. As a result, reliability is good.

Some or all of the first embodiment, the second embodiment, the third embodiment, the fourth embodiment, and modification examples thereof can be randomly combined and used. Further, the contents of the specific scattered radiation component-estimation processing of the first embodiment and the like are exemplary, and scattered radiation component-estimation processing of other aspects can be randomly used. Furthermore, the radiographic image processing devices 30 of the first embodiment and the like can use the radiographic images of a random subject Obj (including a case where a subject is an animal or an object) and a portion to be imaged of a random subject Obj.

A program uses a computer or some elements of a computer to perform a radiographic image acquisition step of acquiring a radiographic image taken from a subject using radiation, a region discrimination step of discriminating a plurality of regions using the radiographic image, a scattered radiation component-estimation step of estimating scattered radiation components of radiation of each region by using scattered radiation component-estimation processing varying for each region, and a scattered radiation component-subtraction step of subtracting the scattered radiation components of each region; and uses a scattered radiation component-estimation section and a scattered radiation component-subtraction section to perform the scattered radiation component-estimation step and the scattered radiation component-subtraction step for each region. Accordingly, the program sequentially estimates and subtracts the scattered radiation components of each region. The program forms the radiographic image processing device 30.

In the embodiments and the like, the hardware structures of processing units, which perform various kinds of processing, such as the region discrimination unit 34, the image processing unit 35, the respective sections of the image processing unit 35, the processing order determination unit 39, and the calculation unit 40, are various processors to be described later. Various processors include: a central processing unit (CPU) that is a general-purpose processor functioning as various processing units by executing software (program); a graphical processing unit (GPU); a programmable logic device (PLD) that is a processor of which the circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a combination of a plurality of FPGAs, a combination of a CPU and an FPGA, a combination of a CPU and a GPU, or the like). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor implementing the functions of the entire system, which includes a plurality of processing units, by one integrated circuit (IC) chip is used as typified by System On Chip (SoC) or the like. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: radiographic imaging system
13: radiation source
14: radiographic imaging panel
15: first radiation detector
16: second radiation detector
17: radiation energy conversion filter
20: console
21: display unit
22: operation unit
30: radiographic image processing device
31: display unit
32: operation unit
33: radiographic image acquisition unit
34: region discrimination unit
35: image processing unit
36: scattered radiation component-estimation section
37: scattered radiation component-subtraction section
39: processing order determination unit
40: calculation unit
51: direct region discrimination section
52: subject region discrimination section
61: direct region-scattered radiation component-estimation section
62: subject region-scattered radiation component-estimation section
81: bed
82: top board
91: scattered radiation component distribution
121: bony part
122: the lungs
123: heart
126: muscle
127: fat
153: separation region discrimination section
154: artifact region discrimination section
155: irradiation-outside region discrimination section
161: neck
162: shoulder
163: head
165: air gap
173: separation region-scattered radiation component-estimation section
174: artifact region-scattered radiation component-estimation section
201: bony part region-discrimination section 202: soft part region-discrimination section
211: bony part region-scattered radiation component-estimation section
212: soft part region-scattered radiation component-estimation section
401: selection unit
B1: primary radiation component
B2: scattered radiation component
G1: first radiographic image
Obj: subject
Ra: radiation
Ra(X1): radiation
S101 to S106: operation step
V1: pixel value
V2: pixel value
X1: direct region
X2: subject region
X3: contact region
X4: separation region

What is claimed is:

1. A radiographic image processing device comprising:
a processor configured to function as:
   a radiographic image acquisition unit that acquires a radiographic image taken from a subject using radiation;
   a region discrimination unit that discriminates a plurality of regions using the radiographic image;
   a scattered radiation component-estimation section that estimates a scattered radiation component of the radiation of each region using scattered radiation component-estimation processing varying for each region;
   a scattered radiation component-subtraction section that subtracts the scattered radiation component of each region; and
   an image processing unit that generates a scattered radiation component-subtracted image where the scattered radiation component has been subtracted by sequentially estimating and subtracting the scattered radiation component of each region using the scattered radiation component-estimation section and the scattered radiation component-subtraction section.

2. The radiographic image processing device according to claim 1,
wherein the processor further configured to function as:
a processing order determination unit that determines an order of the regions in which the image processing unit estimates and subtracts the scattered radiation component.

3. The radiographic image processing device according to claim 2,
wherein the order is an order in which the region where the number of types of scatterers scattering the radiation is smaller is processed earlier.

4. The radiographic image processing device according to claim 3,
wherein in a case where the region discrimination unit discriminates a direct region where the radiation directly reaches a radiation detector without being transmitted through the subject and a subject region where the radiation reaches the radiation detector through the subject, and
the image processing unit generates a direct region-scattered radiation component-subtracted image by subtracting the scattered radiation component of the direct region from the radiographic image and generates a subject region-scattered radiation component-subtracted image by further subtracting the scattered radiation component of the subject region from the direct region-scattered radiation component-subtracted image.

5. The radiographic image processing device according to claim 4,
wherein the region discrimination unit divides the subject region into a bony part region including a bony part and a soft part region including a soft part tissue and discriminates the bony part region and the soft part region, and
the image processing unit subtracts the scattered radiation component of the bony part region from the direct region-scattered radiation component-subtracted image, and further subtracts the scattered radiation component of the soft part region from the direct region-scattered radiation component-subtracted image where the scattered radiation component of the bony part region has been subtracted.

6. The radiographic image processing device according to claim 4,
wherein the region discrimination unit divides the subject region into a bony part region including a bony part and a soft part region including a soft part tissue and discriminates the bony part region and the soft part region, and
the image processing unit subtracts the scattered radiation component of the soft part region from the direct region-scattered radiation component-subtracted image, and further subtracts the scattered radiation component of the bony part region from the direct region-scattered radiation component-subtracted image where the scattered radiation component of the soft part region has been subtracted.

7. The radiographic image processing device according to claim 6,
wherein the region discrimination unit divides the soft part region into regions according to composition and discriminates the divided regions.

8. The radiographic image processing device according to claim 1,
wherein the region discrimination unit discriminates a separation region where the subject is separated from a radiation detector taking the radiographic image.

9. The radiographic image processing device according to claim 1,
wherein the region discrimination unit discriminates an artifact region where an artifact mounted on the subject or included in the subject is present.

10. The radiographic image processing device according to claim 1,
wherein the region discrimination unit discriminates a region outside a region irradiated with radiation.

11. The radiographic image processing device according to claim 1,
wherein the processor further configured to function as:
a selection unit that selects the scattered radiation component-estimation processing for each region.

12. The radiographic image processing device according to claim 11,
wherein the selection unit automatically selects the scattered radiation component-estimation processing to be applied to the region using a position, a size, a shape, and/or a density of the region.

13. The radiographic image processing device according to claim 11, wherein the selection unit accepts selection of the scattered radiation component-estimation processing to be applied to each region.

14. A radiographic image processing method comprising:

a radiographic image acquisition step of causing a radiographic image acquisition unit to acquire a radiographic image taken from a subject using radiation;

a region discrimination step of causing a region discrimination unit to discriminate a plurality of regions using the radiographic image;

a scattered radiation component-estimation step of causing a scattered radiation component-estimation section to estimate a scattered radiation component of the radiation of each region using scattered radiation component-estimation processing varying for each region; and a scattered radiation component-subtraction step of causing a scattered radiation component-subtraction section to subtract the scattered radiation component of each region, wherein the image processing unit sequentially estimates and subtracts the scattered radiation component for each region by performing the scattered radiation component-estimation step and the scattered radiation component-subtraction step for each region using the scattered radiation component-estimation section and the scattered radiation component-subtraction section, and generates a scattered radiation component-subtracted image where the scattered radiation component has been subtracted.

* * * * *